US011467110B2

(12) United States Patent
König

(10) Patent No.: US 11,467,110 B2
(45) Date of Patent: Oct. 11, 2022

(54) METHOD FOR OPERATING A SENSOR DEVICE

(71) Applicant: TDK CORPORATION, Tokyo (JP)

(72) Inventor: Matthias König, Munich (DE)

(73) Assignee: TDK CORPORATION, Tokyo (JP)

( * ) Notice: Subject to any disclaimer, the term of this patent is extended or adjusted under 35 U.S.C. 154(b) by 599 days.

(21) Appl. No.: 16/574,434

(22) Filed: Sep. 18, 2019

(65) Prior Publication Data

US 2020/0088669 A1 Mar. 19, 2020

(30) Foreign Application Priority Data

Sep. 18, 2018 (DE) .......................... 102018122860.0

(51) Int. Cl.
*G01N 27/16* (2006.01)
*G01N 25/18* (2006.01)
*G01N 33/00* (2006.01)

(52) U.S. Cl.
CPC ............. *G01N 27/16* (2013.01); *G01N 25/18* (2013.01); *G01N 33/0062* (2013.01)

(58) Field of Classification Search
CPC ..... G01N 27/16; G01N 25/18; G01N 33/0062
USPC .......................................................... 702/24
See application file for complete search history.

(56) References Cited

U.S. PATENT DOCUMENTS

| 4,019,316 | A | 4/1977 | Pfefferle | |
|---|---|---|---|---|
| 5,834,627 | A * | 11/1998 | Ricco | G01N 27/16 73/23.31 |
| 9,063,105 | B2 | 6/2015 | Berndt et al. | |
| 2008/0173065 | A1 * | 7/2008 | Woodford | G01N 21/274 702/100 |

(Continued)

FOREIGN PATENT DOCUMENTS

| DE | 3839414 A1 | 5/1990 | |
|---|---|---|---|
| DE | 102013008425 B3 | 5/2014 | |
| GB | 2516893 A * | 2/2015 | ........... G01N 33/007 |

OTHER PUBLICATIONS

Brauns, E. et al: "A fast and sensitive catalytic gas sensors for hydrogen detection based on stabilized nanoparticles as catalytic layer," Sensors and Actuators B: Chemical, The 17th International Conference on Solid-State Sensors, Actuators and Microsystems, Jun. 16-20, 2013, pp. 895-903, Elsevier B.V., Barcelona, Spain.

(Continued)

*Primary Examiner* — Nathaniel T Woodward
(74) *Attorney, Agent, or Firm* — Slater Matsil, LLP

(57) ABSTRACT

A method for operating a sensor device for measuring a concentration of a gas species in a gas is disclosed. In an embodiment, the method includes recording a set of data points by performing a plurality of measurements of a temperature sensor element reading, wherein each of the measurements is performed with a different heater setting of the first pellistor element and each of the measurements results in a data point of the set of data points, performing a curve fit of an evaluation function to the set of data points, (Continued)

wherein the evaluation function comprises a first function and a second function, wherein the first function is based on an ideal behavior of the first pellistor element, and wherein the second function is a temperature-dependent steadily rising or steadily falling function and determining the concentration of the gas species in the gas from the curve fit.

11 Claims, 5 Drawing Sheets

(56) References Cited

U.S. PATENT DOCUMENTS

2015/0075256 A1    3/2015  Basham et al.
2019/0316941 A1*  10/2019  König ................. G01D 11/245

OTHER PUBLICATIONS

Nishibori, Maiko et al.: "Thermoelectric hydrogen sensors using Si and SiGe thin films with a catalytic combustor," Journal of the Ceramic Society of Japan, Nov. 25, 2009, pp. 188-192.

Nuscheler, F.: "An investigation of the dynamic behaviour of a silicon microcalorimeter," Science Direct, Sensors and Actuators, May 1989, 2 pages, vol. 17, Issues 3-4, Elsevier B.V.

Reimann, Peter et al.: "Sensor Arrays, Virtual Multisensors, Data Fusion, and Gas Sensor Data Evaluation," Gas Sensing Fundamentals, Springer Series on Chemical Sensors and Biosensors, Jun. 16, 2013, pp. 67-107.

SGX Sensortech: "MP-7217-TC," Pellistors (VQ) from SGX Sensortech, Combined Pellistor and TC Sensor, Sep. 9, 2019, 2 pages.

Shamsi, Abolghasem: "Partial oxidation of methane and the effect of sulfur on catalytic activity and selectivity," Catalysis Today 139, U.S. Department of Energy, National Energy Technology Laboratory (NETL), May 15, 2018, pp. 268-273, Elsevier B.V.

* cited by examiner

METHOD FOR OPERATING A SENSOR DEVICE

CROSS-REFERENCE TO RELATED APPLICATIONS

This application claims the priority of German patent application 102018122860.0, filed on Sep. 18, 2018, which application is hereby incorporated herein by reference.

TECHNICAL FIELD

Embodiments of the present invention are related to a method for operating a sensor device.

BACKGROUND

A possibility of a miniaturized gas sensor for consumer mass market applications is the so called pellistor. There are two types of pellistors, catalytic and thermal conductivity pellistors, operating in different modes. The catalytic type pellistor works by burning the gas. The heat generated by the burning process is proportional to the gas concentration. The thermal conductivity pellistor measures the heat conductivity of the surrounding gas which includes the gas concentration information.

However, pellistors can be "poisoned" by contaminants such as silicon compounds, chlorine compounds, heavy metals and sulfur compounds, which react with the pellistor surface, for instance with the catalyst during the burning process, and cause an inert layer building up on the surface. For instance, siloxanes can lead to a layer consisting or comprising of $SiO_2$ and/or components containing one or more of Si, C, H and O. Although such layer severely degrades the ability of the pellistor to detect gas, it is not at all evident during normal operation. In order to reduce the poisoning effect, filters are used in the state of the art, which can prolong the life span of the pellistor, during which the pellistor works properly. However, as soon as a filter of a pellistor becomes saturated, the sensitivity will degrade.

SUMMARY

Embodiments provide a method for operating a sensor device, preferably a sensor device for measuring information about a concentration of at least one gas species in a gas.

According to at least one embodiment, in a method for operating a sensor device the sensor device is used for measuring a concentration of at least one gas species in a gas. The gas can be preferably the gas atmosphere surrounding the sensor device. The term "measuring a concentration" includes measuring information, i.e., for instance an output signal of the sensor device, which is directly or indirectly related to the concentration. In particular, at least during one method step of the method the sensor device is at least partly in contact with the gas. This means that at least one component of the sensor device is in contact with the gas.

According to a further embodiment, in the method a sensor device is used which comprises at least one pellistor element. In particular, the at least one pellistor element can be or comprise a first pellistor element. Accordingly, the sensor device can comprise one pellistor element which is the first pellistor element. During at least one method step the first pellistor element can be in contact with the gas. Measuring at least one output signal of the sensor device, which can be an output signal of the first pellistor element, can provide information related to the gas. Consequently, here and in the following the first pellistor element can also be denoted as active pellistor element. Furthermore, the sensor device can comprise a second pellistor element as described further below, so that the sensor device can comprise two pellistor elements. It is also possible that the sensor device comprises more than two pellistor elements. In cases where the sensor device comprises more than one pellistor element, the more than one pellistor element can be monolithically integrated on a common substrate as described further below, or can be embodied as separate components.

According to a further embodiment, at least one or more and preferably all pellistor elements of the sensor device comprise a heater element and a temperature sensor element, respectively. The following description of components and features of a pellistor element as well as of modes of operating a pellistor element applies to one or more or preferably all of the pellistor elements of the sensor device. In particular, the following description can apply to the first pellistor element or to the second pellistor element or to each of the first and the second pellistor elements. In embodiments where the sensor device comprises more than one pellistor element, the more than one pellistor elements can be embodied similarly or differently, i.e., the pellistor elements can comprise similar components and/or different components, which are described in the following.

When operated, the heater element can increase the temperature of the pellistor element, which means that the heater element can increase the temperature of at least a part of the pellistor element. The temperature sensor element can be embodied to measure the temperature of the pellistor element or of at least a part of the pellistor element.

The sensor device can have electrical contacts for contacting the one or more pellistor elements of the sensor device. In particular, the sensor device can have electrical contacts for contacting the heater element and the temperature sensor element of the one or more pellistor elements, respectively. At least some of the electrical contacts can be embodied for measuring an output signal of the respective pellistor element and, in particular, of the temperature sensor element. The output signal can preferably be an electrical property as, for example, an electrical resistance, an electrical current and/or an electrical voltage.

According to a further embodiment, the heater element is embodied as a heating filament or heating wire and, in particular, as a heating resistance. Preferably, the heater element comprises or is made of a noble metal as, for example, Pt. Other metals, for example W, are also possible in addition or alternatively.

According to a further embodiment, the temperature sensor element comprises a material which changes its electrical resistance depending on its temperature. For example, the temperature sensor element can comprise a thermistor material, i.e., an NTC (negative temperature coefficient) material or a PTC (positive temperature coefficient) material. Furthermore, the temperature sensor element can comprise a noble metal and/or one or more metal oxides. For example, the noble metal comprises or is Pt. By measuring an output signal of the temperature sensor element, for example, by measuring the electrical resistance, information about the temperature of at least a part of the pellistor element can be measured. By means of a calibration of the output signal, for instance the electrical resistance, in relation to the temperature, the temperature can be directly extracted from the temperature sensor element output.

According to a further embodiment, the heater element is the temperature sensor element. In other words, the heater element and the temperature sensor element can be one and the same component, which can be used at the same time for heating the pellistor element and, for example, by measuring its temperature-dependent electrical resistance, for measuring the temperature. Alternatively, the heater element and the temperature sensor element can be embodied as two different components. Such a pellistor element can be denoted as a microcalorimeter. The advantage of such a design can be a higher sensitivity of the temperature sensor element to temperature changes compared to the heater element, so that forming the heater element and the temperature sensor element as different components can provide a higher measuring accuracy.

According to a further embodiment, the sensor device comprises a substrate. The substrate can carry the one or more pellistor elements of the sensor device. In cases where the sensor device comprises more than one pellistor element, the substrate can be a common substrate, carrying all of the pellistor elements of the sensor device. Alternatively, each of the pellistor elements of the sensor device can have its own substrate. Preferably, the substrate comprises silicon. The temperature sensor element of the pellistor element or, in cases of more than one pellistor element, preferably the temperature sensor element of each of the pellistor elements of the sensor device can be arranged in or on a membrane, which is arranged on the substrate. Alternatively or additionally, in cases where the temperature sensor element and the heater element are different components, also the heater element of the pellistor element and, in cases of more than one pellistor element, preferably of each of the pellistor elements can be arranged in or on the membrane. In the case that at least one pellistor element of the sensor device comprises a catalyst element as described below, the catalyst element can be arranged on the membrane in order to have contact to the gas. The membrane of the sensor device comprises or is made of an electrically insulating material, for instance silicon oxide and/or silicon nitride, and at least partly or substantially completely encloses the heater element and/or the temperature element. The substrate and/or the membrane with the components arranged in the membrane can be manufactured by standard MEMS (microelectromechanical systems) technology, thereby providing small dimensions and a high degree of integration. For example, when forming the membrane with the temperature sensor element and/or the heater element, lithographic process steps can be used.

According to a further embodiment, the pellistor element or each of the more than one pellistor elements of the sensor device, which can comprise or be, as described above, the first pellistor element or the second pellistor element or each of the first and second pellistor elements, is embodied as a catalytic type (CT) pellistor or as a thermal conductivity (TC) pellistor. A pellistor element embodied as a catalytic type pellistor element comprises a catalyst element and, when operated by heating at least the catalyst element by means of the heater element, works by burning a gas to be examined (target gas) on the surface of the catalyst element. The additional heat that is generated by the gas combustion process on the surface of the catalyst element can be detected by means of the temperature sensor element and preferably can be used to produce a sensor signal that is proportional to the gas concentration. The catalyst element can comprise a metal oxide. The metal oxide can for instance comprise Al and/or Pt. For example, the catalyst element can comprise or consist of platinum oxide and/or aluminum oxide or aluminum oxide mixed with platinum. In case of a TC pellistor element, the catalyst element is missing. The temperature sensor element of the TC pellistor element, when operated by heating the pellistor element by means of the heater element with a certain power, for instance with a constant heating voltage, measures a temperature of the pellistor element which is influenced by the heat conductivity of the gas to be examined, since the target gas changes the heat conductivity of the surrounding air. In short, the TC pellistor element can be used to measure a gas concentration via detecting information about the heat conductivity of the surrounding gas atmosphere. For example, the heat conductivity of air decreases with an increasing $CO_2$ concentration.

Both sensor principles have in common that the effects can be very small, in particular in the case of gas concentrations in the ppm range. As all heated gas sensors, the sensor device and, in particular, at least the first pellistor element of the sensor device can have the problem of poisoning as mentioned above. For example, in the case of silicon poisoning, silicon containing organic molecules like hexamethyldisiloxane (HMDS), which can, for example, as a contaminant, be part of the gas in contact with the sensor device, are decomposed on the heated sensor device surface, thereby leaving an $SiO_2$ layer, which builds up with time and which influences the sensor device. In particular, the poisoning layer can provide for instance a cooling effect that leads, at a certain heater element power and a certain gas atmosphere, to a different pellistor element temperature and, consequently, to a different temperature sensor element reading compared to an identical sensor device under those same conditions but without a poisoning layer. Thus, the poisoning effect can be misinterpreted as a change in the gas atmosphere.

According to a further embodiment, the method for operating the sensor device comprises a method step in which more than one measurement are taken. In particular, a plurality of measurements is taken at least with the first pellistor element, wherein each of the measurements is performed with a different heater setting of at least the heating element of the first pellistor element. The different heater settings can correspond to different heating voltages and/or different heating currents. Consequently, for each of the plurality of measurements a different voltage and/or a different current is applied to the heater element. Thus, for each of the measurements the heater element of at least the first pellistor element can be operated with a different heating power, which can result in different temperatures of at least the first pellistor element. The heater setting can be changed continuously or in discrete steps from measurement to measurement. In particular, a fixed number of measurements can be taken at several different heating voltages of the heater element, for instance 0 V, 1.5 V and 3 V. The number of measurements can also be more than three.

In each of the measurements, a temperature sensor element reading is taken. In other words, for each heater setting the output of the temperature sensor element of at least the first pellistor element is used for measurement. Either the output signal of the temperature sensor element or a value calculated from the measured output signal, which, as explained above, can be related to the temperature of the first pellistor element, can be stored in a data processor together with the corresponding heater-setting-related value, which can for instance be the voltage, the current or the power applied to the heater element. Consequently, the method can comprise a method step A, in which a set of data points is recorded by performing a plurality of measurements of a temperature sensor element reading, wherein each of the measurements is performed with a different heater setting of at least the first pellistor element and wherein each of the measurements results in a data point of the set of data points. In other words, a continuous or stepwise temperature sweep is performed by changing the heater setting in a heater setting sweep, during which a temperature sensor element reading is recorded continuously or stepwise. During method step A, at least the first pellistor element is in contact with the target gas and, depending on its design, is operated in the CT mode or in the TC mode as explained above.

When no poisoning layer is present on the surface of the first pellistor element, the first pellistor element shows, as any pellistor, depending on the pellistor element setup, the surrounding gas atmosphere, which can be the target gas, a certain behavior in a temperature sweep, i.e., a certain non-linear dependency of the temperature sensor element reading, when measurements are taken with different heater settings in the same gas atmosphere. In other words, due to the physics of the interaction of the target gas with the pellistor element in a constant gas atmosphere, the temperature sensor element reading, which can be plotted in a diagram depending on the heater setting, changes non-linearly with changes of the pellistor element temperatures. Typically, substantially three different regions can be identified in such diagrams. For example, when the heating power and thus the temperature of a CT pellistor element is increased starting from room temperature, the reaction rate at the catalyst element, and thus the heat produced by the reaction, starts at a certain pellistor temperature, indicating the temperature at which the burning process starts. Since the reaction rate of the gas at the catalyst element is controlled by surface kinetics at low temperatures, the reaction rate and thus the temperature then steadily increases with increasing heating power in a first range, corresponding to a surface-kinetics-controlled region in the diagram. When further increasing the heating power, the increase in reaction rate and thus also the increase in temperature slows down or even decreases in a second range, since for higher heating powers and thus higher induced temperatures the reaction rate is controlled by mass diffusion, corresponding to a mass-diffusion-controlled region in the diagram. When even further increasing the heating power, the reaction rate and thus the temperature again steadily increases with increasing heating power in a third range, corresponding to a catalytically-supported homogenous reaction region. The same dependency applies to other heater settings as heating voltage or heating current. The non-linear dependency is theoretically well-known in the art, for example, as explained in prior art document U.S. Pat. No. 4,019,316 A. TC pellistor elements show a similar behavior. The described heater-setting-dependent pellistor element behavior in absence of the poisoning effect, which can be denoted as ideal behavior, can be calculated and/or measured for a pellistor element and a target gas. In particular, the ideal behavior of the first pellistor element can be calculated or recorded for instance in a controlled gas atmosphere and in the absence of a poisoning layer.

The presence of a poisoning layer usually leads, as explained above, to a cooling effect. For example, the poisoning layer can increase the heat flow from the heater element for example, to the substrate. Additionally or alternatively, the poisoning layer can have a greater roughness than other components of the sensor device and can provide a better thermal coupling to the surrounding atmosphere. Furthermore, the poisoning layer can at least partly cover the active surface of the catalyst element and thus reduce the reaction rate in the burning process at the catalyst element. The higher the pellistor element temperature, the greater is also the cooling effect of the poisoning layer, so that the poisoning effect can be characterized by a steadily rising heater-setting dependency. In short, the higher the temperature of the pellistor element, the stronger is also the cooling influence of the poisoning effect, so that the poisoning effect can be characterized by a heater-setting-dependent drift. Furthermore, as the thickness of the poisoning layer can increase with operation time of the sensor device, the contribution of the cooling effect can increase in a sort of aging process.

According to a further embodiment, in a further method step B a curve fit is performed, in which an evaluation function is fitted to the set of data points. The evaluation function comprises a first function and a second function. The first function is a function based on the ideal behavior of the first pellistor element. The ideal behavior can, as described above, be based on a theoretical model and/or on measurements in a clean gas, which can be performed once before the sensor device is normally operated and can be recorded and stored in a data processor. The second function is a temperature-dependent steadily rising or steadily falling function, for example, a liner function, a polynomial function, an exponential function or a combination thereof, which takes into account the poisoning effect as described above. As is well known, a curve fit is the process of constructing a curve or mathematical function which can be subject to constraints and which has the best fit to a series of data points. In the method described here, the constraints can be determined by the first and the second function. The curve fit can comprise any suitable mathematical evaluation, for example, a least-squares fit or the use of a neuronal network.

In a further method step C, the concentration of the gas species in the gas can be determined from the curve fit, since the fit makes it possible to separate the poisoning effect from the ideal behavior by means of analyzing the contributions of the first and second functions in the curve fit. This can be possible in particular since the first function and thus the evaluation function can be different from a steadily rising or steadily falling function.

According to a further embodiment, each of the data points comprises a calibrated temperature sensor element reading. In particular, as explained above, the calibrated temperature sensor reading can incorporate the temperature dependency of the measured electrical property of the temperature sensor element, which can be non-linear. The calibration can be done in a clean gas such as clean air and in the absence of a poisoning layer by measuring the temperature sensor element reading for different heater settings. The calibrated temperature sensor element reading can result in a so-called baseline, which corresponds to a constant value independent of the heater setting. Measured shifts in the baseline can then be caused by changes in the gas atmosphere and/or a drift due to the poisoning effect.

According to a further embodiment, the sensor device comprises a second pellistor element, which is used as a reference pellistor element. Features and method steps explained above in connection with the first pellistor element can also apply to the second pellistor element. In particular, the second pellistor element comprises a heater element and a temperature sensor element. The second pellistor element can be operated simultaneously with the first pellistor element during method step A. Accordingly, an output signal of the second pellistor element can be recorded during method step A by performing a plurality of measurements of a temperature sensor element output signal of the second pellistor element, wherein each of the measurements is performed at a different heater setting of the second pellistor element. In particular, the step of performing a plurality of measurements of a temperature sensor element reading in method step A can include measuring a differential signal of the output signals of the temperature sensor element of the first pellistor element and of the temperature sensor element of the second pellistor element. The differential signal can be provided by a voltage divider as, for instance, a Wheatstone Bridge containing the first and second pellistor elements. The output signal of the second pellistor element in combination with the output signal of the first pellistor element can be used for compensating undesired variations of the environment, such as humidity and/or temperature variations, and/or undesired variations of the operating parameters of the sensor device, such as undesired heater setting variations. For instance, the heater elements of the first and second pellistor elements can be operated in parallel with the same heater settings, so that the second pellistor element can, for example, be used to compensate undesired heater setting variations during method step A, for example, heating voltage variations during the temperature sweep.

Furthermore, the second pellistor element can be similar to the first pellistor element and, during method step A, can be operated in clean air or in a vacuum. In other words, the second pellistor element can be embodied in the same way as the first pellistor element, for instance as a CT or TC pellistor element, but without contact to the target gas at least during method step A. Both pellistor elements can be operated simultaneously with the same heater settings during methods step A. As both pellistor elements react similarly to environmental temperature changes, only gas-related information can be included in the combined reading of the pellistor element outputs. It can be possible that there is a little temperature difference between the first and second pellistor elements, which, however, can be cancelled by a temperature calibration, which can be done before performing the first method step.

Furthermore, it can be possible that during method step A for each measurement the heater element of the first pellistor element heats the first pellistor element to a first temperature and the heater element of the second pellistor element heats the second pellistor element to a second temperature that is different from the first temperature. In this regard, the heater elements of the first and second pellistor elements can be embodied in such way that in each measurement the same heating voltage, which is varied from measurement to measurement for the temperature sweep, can be applied to both heater elements. The temperature sensor elements of the first and second pellistor elements can be configured such that the temperature sensor element of the first pellistor element provides a temperature sensor element reading at the first temperature that is similar to the temperature sensor element reading of the temperature sensor element of the second pellistor element at the second temperature. With such a setup, it can be possible to cancel small heating voltage variations during the temperature sweep. In this case, the second pellistor element can be in contact with the target gas at least during method step A.

The method described herein provides a possibility to identify the poisoning effect in the measurements and to correct the measurements accordingly in order to obtain information of the target gas. In particular, the method makes it possible to distinguish between effects caused by the target gas and by the poisoning effect on the sensor device output, so that the sensor device can work longer according to its specifications even in the presence of poisoning layers. Furthermore, since a plurality of measurements is performed in a temperature sweep in the described method, it can be possible to measure absolute gas concentrations instead of relative gas concentrations or at least to get better relative results compared to the measurement methods in the state of the art, in which measurements are taken only at a fixed heater setting.

BRIEF DESCRIPTION OF THE DRAWINGS

Further features, advantages and expediencies will become apparent from the following description of exemplary embodiments in conjunction with the figures.

In the figures, elements of the same design and/or function are identified by the same reference numerals. It is to be understood that the embodiments shown in the figures are illustrative representations and are not necessarily drawn to scale.

In the following, specific details are set forth, such as features of the method for operating the sensor device and of the sensor device as well as advantageous effects thereof, in order to provide a thorough understanding of embodiments of the invention. It will be apparent to one skilled in the art that embodiments of the invention may be practiced without these specific details.

DETAILED DESCRIPTION OF ILLUSTRATIVE EMBODIMENTS

Figure 1:
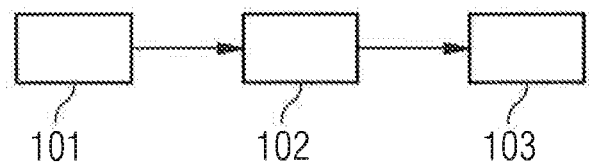
FIG. 1 illustrates method steps of a method for operating a sensor device according to an embodiment.

FIG. 1 shows a method of operating a sensor device according to an embodiment. In particular, the method is a method for measuring a concentration of a gas species in a gas. The method comprises in general a method step 101, which corresponds to method step A described in the general part, in which a set of sensor values is measured by varying a sensor setting, wherein each of the sensor values is associated to a particular sensor setting, the measurement resulting in a set of a plurality of data points. Each data point represents a sensor setting and an associated sensor value. The method further comprises a method step 102, which corresponds to method step B described in the general part, in which a curve fit of an evaluation function to the plurality of data points is performed, wherein the evaluation function comprises an ideal-behavior function related to an ideal behavior of the sensor device and a poisoning-effect-related function related to a poisoning effect, which can be caused by at least one poisoning layer that can build up on the sensor device surface with time. In particular, the two functions show different dependencies with regard to the sensor setting. By means of the curve fit it can be possible in a third method step 103, which corresponds to method step C described in the general part, to distinguish between the poisoning effect and the influence of the gas on the sensor device measurement, so that information related to the gas can be extracted from the measurements.

In particular, the sensor device comprises at least a first pellistor element in contact with the gas, wherein the first pellistor element comprises a heater element and a temperature sensor element. In the first method step 101, a set of data points is recorded by performing a plurality of measurements of a temperature sensor element reading, wherein each of the measurements is performed with a different heater setting of the first pellistor element and each of the measurements results in a data point of the set of data points. In method step 102, a curve fit of an evaluation function to the set of data points is performed, wherein the evaluation function comprises a first function and a second function. The first function is based on an ideal behavior of the first pellistor element, while the second function is a temperature-dependent steadily rising or steadily falling function. In method step 103, the relative or absolute concentration of the gas species in the gas is determined from the curve fit.

Further details, features and embodiments of the method are explained in connection with the following figures.

Figure 2A:
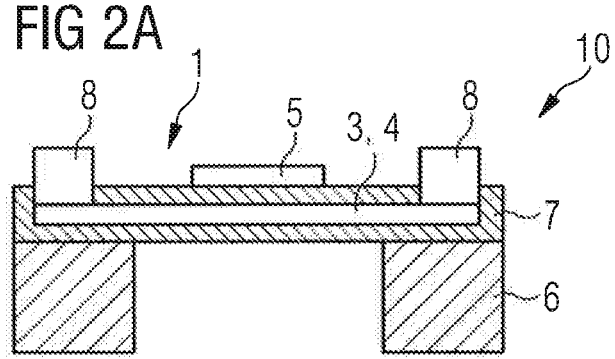
FIGS. 2A to 4 show sensor devices according to further embodiments.
Figure 2B:
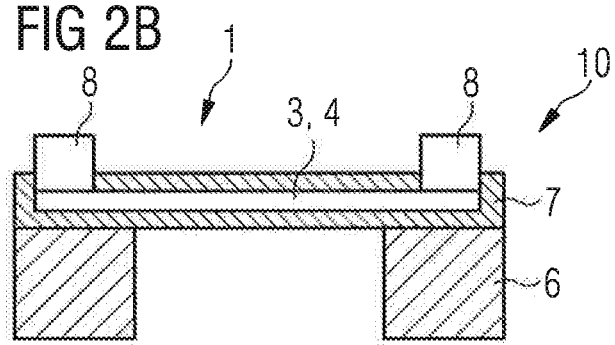
Figure 2C:
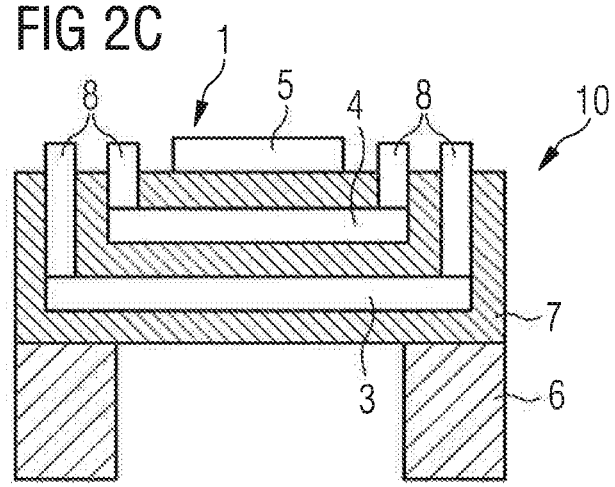

FIGS. 2A to 2C illustrate exemplary embodiments of a sensor device 10. In the embodiments of all of FIGS. 2A to 2C, the sensor device 10 comprises a first pellistor element 1 with a heater element 3 and a temperature sensor element 4, respectively.

According to the embodiment of FIG. 2A, the heater element 3 is the temperature sensor element 4, meaning that the heater element 3 and the temperature sensor element 4 are embodied as one and the same component, which can also be denoted as a combined heater and temperature sensor element 3, 4 in the following. The combined heater and temperature sensor element 3, 4 comprises a filament, which, on the one hand, acts as a resistance heater upon application of a sufficiently high electrical current. For concentrating the produced heat in a desired area, a part of the filament can be formed in a meander-like shape. On the other hand, the filament changes its electrical resistance depending on its temperature, so that measuring the electrical resistance, or an electrical property depending on the electrical resistance, can provide information about the temperature of the combined heater and temperature sensor element 3, 4. For example, an NTC or PTC material can be used for heating and temperature-sensing. For instance, the combined heater and temperature sensor element 3, 4 can comprises a noble metal as, for example, Pt, which can be used as a heater material and which has a temperature-depending electrical resistance. For providing the electrical current to the combined heater and temperature sensor element 3, 4 when operated as a heater and/or for measuring an electrical property of the heater and temperature sensor element 3, 4, the first pellistor element 1 comprises electrical contacts 8.

The sensor device 10 shown in FIG. 2A further comprises a substrate 6, which can be made, for example, from silicon. The combined heater and temperature sensor element 3, 4 is at least partly situated in a membrane 7, which can comprise or can be made of silicon oxide and/or silicon nitride and which can at least partly enclose the combined heater and temperature sensor element 3, 4. The membrane 7 has a thickness in the range of about 400 nm to 10 µm. The substrate 6 has openings in the regions where the combined heater and temperature sensor element 3, 4 is situated so that the thermal mass of the first pellistor element 1 can be very low. The substrate 6 and/or the membrane 7 with the components arranged in the membrane 7 can be manufactured by standard MEMS (microelectromechanical systems) technology, thereby providing small dimensions of typically 2×2 mm² or even less and a high degree of integration.

The first pellistor element 1 of the embodiment shown in FIG. 2A is embodied as a catalytic type (CT) pellistor and comprises a catalyst element 5 in the form of a pellet on the membrane 7. In particular, the catalyst element 5 can be arranged on the meander-shaped part of the combined heater and temperature sensor element 3, 4, so that the catalyst element 5 can be effectively heated. The catalyst element 5 comprises or consists of a metal oxide, for instance an oxide with Al and/or Pt. For example, the catalyst element 5 can comprise or consist of platinum oxide and/or aluminum oxide or aluminum oxide mixed with platinum. When an electrical voltage and/or an electrical current is applied to the heater element 3, the first pellistor element 1 is heated to a temperature above room temperature. When heated to a temperature of typically at least 150° C. to about 300° C., the catalyst element 5 can combusts gas, i.e., for example, at least one gas species contained in the gas, surrounding the first pellistor element 1, thereby generating additional heat. That additional heat increases the temperature of the first pellistor element 1. Consequently, the combustion-generated additional heat produces a change in the electrical resistance of the temperature sensor element 4 of the first pellistor element 1, which can be related, for instance proportional, to the concentration of the at least one gas species.

In contrast to the embodiment shown in FIG. 2A, the sensor device 10 according to the embodiment shown in FIG. 2B is a thermal conductivity (TC) pellistor element, which has no catalyst element. When heating the first pellistor element 1 by means of the heater element 3, which can typically also be in the range of at least 150° to about 300° C., the temperature of the first pellistor element 1, which is measured by means of the temperature sensor element 4, is influenced by the heat conductivity of the gas surrounding the first pellistor element 1. Since a changing concentration of a target gas species changes the heat conductivity of the surrounding gas, information about a concentration of at least the gas species can be detected by measuring information about the heat conductivity of the surrounding gas atmosphere.

Alternatively to the embodiments shown in FIGS. 2A and 2B, the first pellistor element 1 can be embodied as a so-called microcalorimeter and can have a heater element 3 and a temperature sensor element 4, which are separate components, as shown in FIG. 2C. This can provide a higher sensitivity compared to the combined heater and temperature sensor elements of the previous embodiments. The heater element 3 and the temperature sensor element 4 can be embodied as explained above and can all be arranged in or on the membrane 7. As shown, additional contact elements 8 can be provided for contacting the heater element 3 and the temperature sensor element 4 separately. The first pellistor element 1 can be embodied, as shown in FIG. 2C, as a microcalorimeter of the catalytic type with a catalyst element 5. Alternatively, the catalyst element 5 can be missing, so that the microcalorimeter can also be embodied as a TC pellistor element.

For the method step 101 of the method of FIG. 1, the output signal of the temperature sensor element 4 of the shown sensor devices 10 can be used as a temperature sensor element reading, respectively. Alternatively, for instance a calibrated output signal as explained below can be used.

Figure 3:
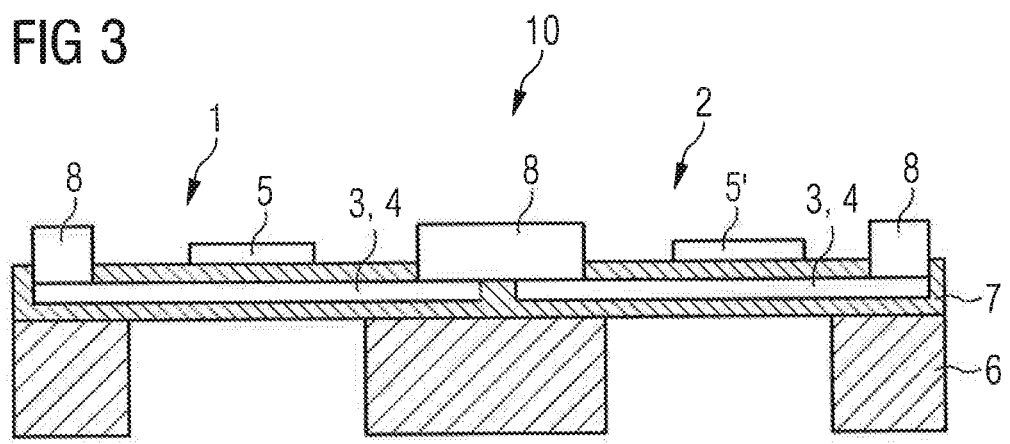

Alternatively to the embodiments of FIGS. 2A to 2C, the sensor device can comprise more than one pellistor element and preferably two pellistor elements, which can be advantageous in order to cancel measurement errors caused by environmental temperature and/or humidity effects. Generally, in a two-pellistor setup at least one pellistor element reacts to the gas, while the other one works as a compensator. This can be ensured by different techniques. For instance, one pellistor element, i.e., the active pellistor element, could be exposed to the gas, whereas the other pellistor element, i.e., the reference or compensator pellistor element, is arranged in a controlled reference gas atmosphere. Another possibility is to provide the active pellistor element with a catalyst element and the reference pellistor element with no catalyst element or with a dummy element. Such a configuration is shown by way of example in FIG. 3, which shows an embodiment of a sensor device 10 which has a second pellistor element 2 in addition to the first pellistor element 1. The second pellistor element 2 is configured similarly to the first pellistor element 1 with a heater element 3 and a temperature sensor element 4 in or on a membrane 7 on a substrate 6 as described in connection with FIGS. 2A to 2C. In particular, as shown in FIG. 3, the first and second pellistor elements 1, 2 can be arranged on a common substrate 6. Only by way of example the first and second pellistor elements 1, 2, are shown comprising a combined heater and temperature sensor element 3, 4, respectively. Alternatively, the first and second pellistor elements 1, 2 can be embodied as microcalorimeters.

The second pellistor element 2 can be used as a reference pellistor element and can be free of a catalyst element. Instead of the catalyst element 5 of the first pellistor element 1, the second pellistor element 2 can have a dummy element 5' as shown in FIG. 3, which for instance resembles in its shape and/or mass the catalyst element 5, but is inert compared to the catalyst element 5, or, alternatively, can be free of the dummy element 5'.

Figure 4:
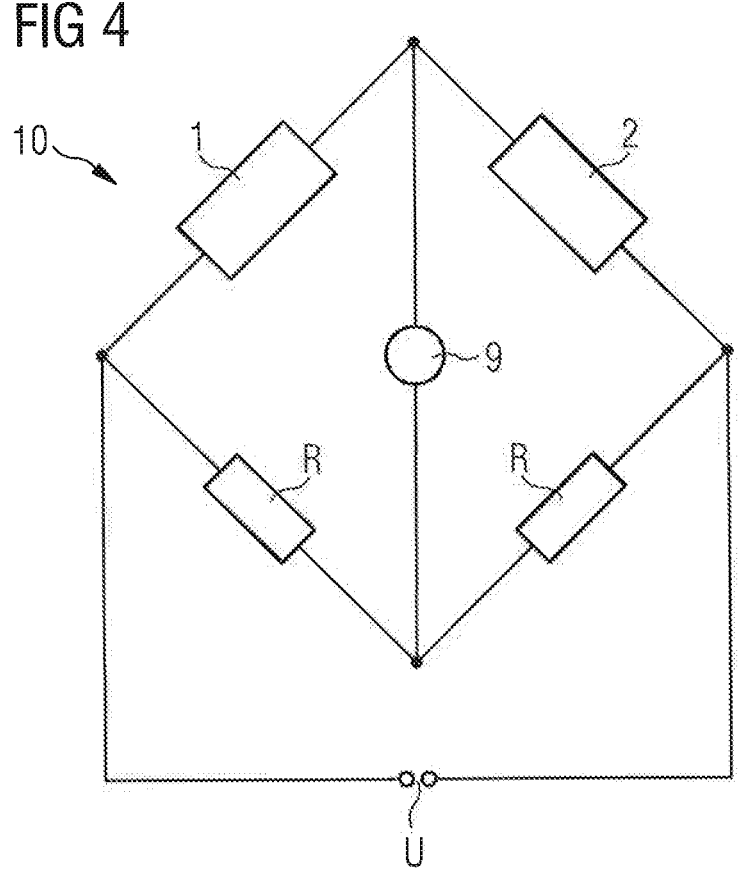

Both the first and the second pellistor element 1, 2 react to environmental temperature and/or humidity changes in the same way. Therefore, the differential signal of the temperature sensor element outputs of the first and the second pellistor elements 1, 2 is constant. In the case of a gas change mainly the active first pellistor element 1 will react by changing its temperature due to the changed burning process at the catalyst element 5, which leads to a change in the output signal of the temperature sensor element 4 of the first pellistor element 1 compared to the second pellistor element 2. By means of a voltage divider circuit the output signal difference can be easily measured, which can provide the temperature sensor element reading in method step 101 of the method of FIG. 1. For example, as shown in FIG. 4, the first and second pellistor elements 1, 2 can be part of a Wheatstone Bridge using the temperature-depending resistances of the temperature sensor elements of the two pellistor elements 1, 2 and additionally comprising two suitable resistors R. With a voltage applied by a voltage source U the balance of the bridge circuit can be measured by means of a measurement device 9. In this case, for the method step 101 of the method shown in FIG. 1 the output signal of the measurement device 9, which can be a voltage meter, can be used as temperature sensor element reading. Alternatively, for instance a calibrated output signal of the measurement device reading can be used as explained below. In the case of an ambient temperature change the pellistor elements 1, 2 will both be cooler or hotter, but as mentioned before the voltage divider circuit can cancel this effect.

In the state of the art usually a constant heater setting is used for the heater element 3 of the one or more pellistor elements of the sensor device. In particular, usually a constant heating voltage is used for operating the heater element(s).

Figure 5A:
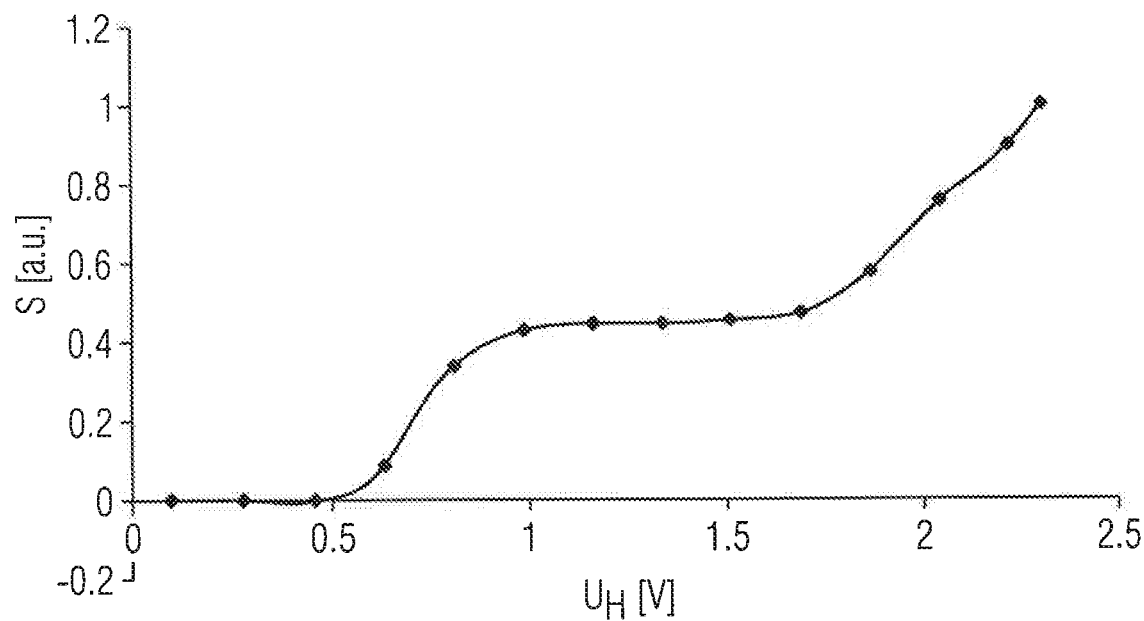
FIGS. 5A and 5B show graphs illustrating an ideal behavior of sensor devices according to further embodiments.
Figure 5B:
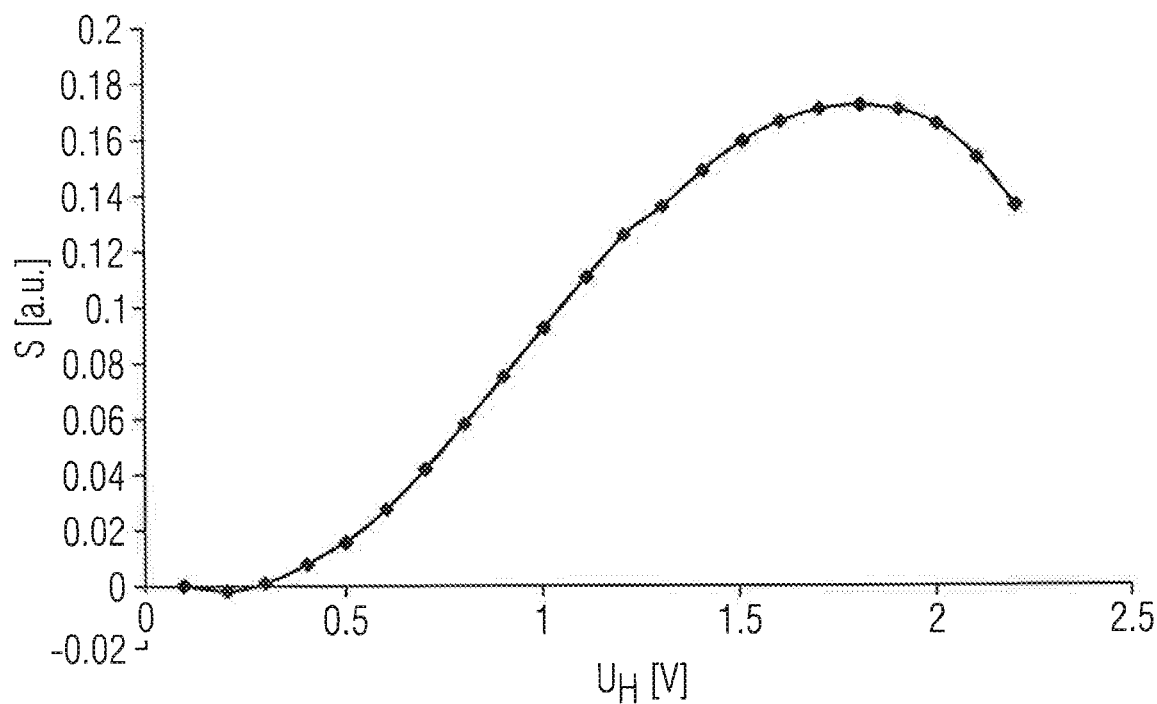

As shown in FIGS. 5A and 5B, the temperature sensor element reading S of sensor devices as explained before depends on the temperature of the pellistor elements and thus on the heater setting, which is exemplarily expressed by the heater voltage $U_H$. In FIG. 5A a sensor device configured as a CT pellistor was used in a gas atmosphere containing a constant concentration of isopropyl alcohol (IPA) vapor, while in FIG. 5B a sensor device configured as a TC pellistor was used in a gas atmosphere containing a constant concentration of 5000 ppm of carbon dioxide ($CO_2$). The heater-setting-dependent temperature sensor element reading S can in both cases be interpreted as a measure for the sensitivity of the respective sensor device to the respective gas species. As explained above in the general part, in the presence of the gas species the temperature sensor element reading S has a non-linear dependency on the temperature and thus on the heater setting due to different physical processes in different temperature ranges. The graph of FIG. 5B shows only the first and second regions, but would also continue for higher heater voltages in a third region as explained above.

As explained above in the general part, the pellistor element(s) of the sensor device can be "poisoned" by contaminants such as silicon, chlorine compounds, heavy metals and sulfur compounds, which can react with the pellistor surface and which can lead to a poisoning layer that negatively influences the sensor properties. By way of example, FIG. 6A illustrates the sensor device 10 of FIG. 3 with such poisoning layers 11 on the pellistor elements 1, 2.

Figure 6A:
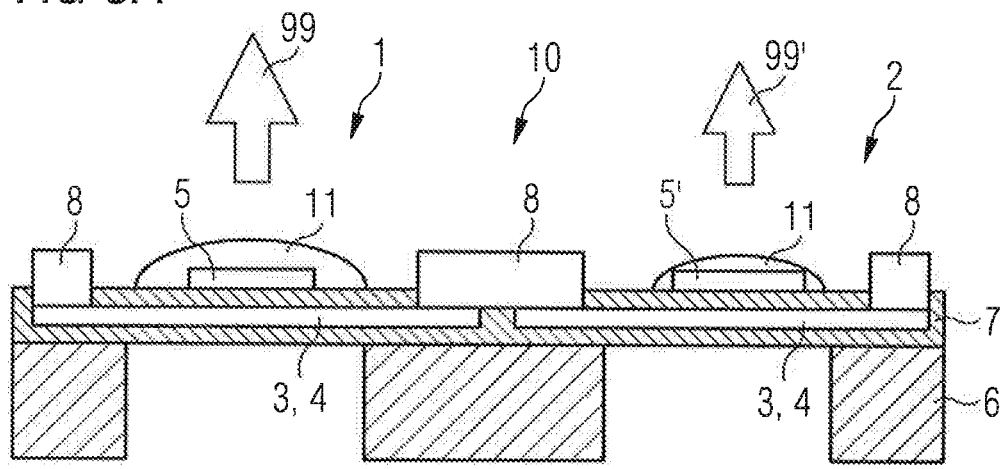
FIGS. 6A and 6B illustrate the effect of a sensor device with poisoning layers.
Figure 6B:
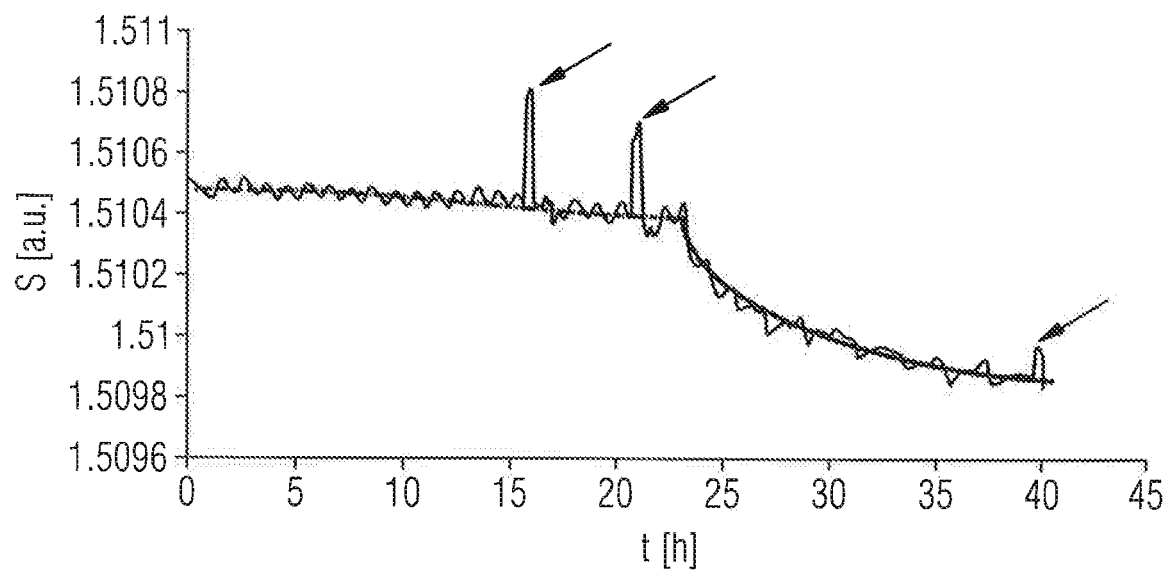

In order to illustrate the poisoning effect, FIG. 6B shows the temperature sensor element reading S of the same sensor device as in FIG. 5A, which was subjected to several gas atmospheres during a time t. In particular, in the first 5 hours the gas atmosphere was clean air. Between t=5 h and t=23 h, the gas atmosphere additionally contained vapor of a silicone glue, while for times t>23 h the gas atmosphere contained vapor of trimethyldisiloxane (TMDS). The three peaks marked by the arrows were caused by temporary additions of 300 ppm carbon monoxide (CO). As can be easily seen, the addition of siloxane vapors leads to a poisoning-caused drift in the temperature sensor element reading S, thereby decreasing the sensitivity of the sensor device, wherein different siloxanes may lead to different drift gradients.

As explained in the general part, a poisoning layer can, depending for example, on its thickness, change for instance the heat flow to the surroundings, as indicated in FIG. 6A by arrows 99 and 99', which causes an increased cooling effect and results in the drift behavior. In particular, it can be possible that the active and the reference pellistor elements as the pellistor elements 1, 2 of the sensor device 10 in FIG. 6A are affected by the poisoning not in the same way but differently, which is indicated by the different sizes of the poisoning layers 11, if, for instance due to different reaction rates and/or different temperatures during operation. For example, in the case of an active CT pellistor element there will be a creation of a thicker $SiO_2$ layer in the case of the described siloxane-containing atmospheres due to the catalyst element in comparison to a reference pellistor element without a catalyst element, as the catalyst intensifies the reaction of siloxane to $SiO_2$, resulting in an increased heat distribution to the substrate and the atmosphere compared to the reference pellistor element without a catalyst element. This can lead to the negative drift as shown in FIG. 6B. In the case of an active TC pellistor element there is also an effect caused by different reaction rates, since the active pellistor element and the reference pellistor element are usually operated at different temperatures, and the reaction of siloxane to $SiO_2$ is increased with higher temperature. For example, if the active TC pellistor element is operated at a temperature lower than the temperature of the reference pellistor element, for instance 150° C. compared to 300° C., the drift would be positive.

Figure 7:
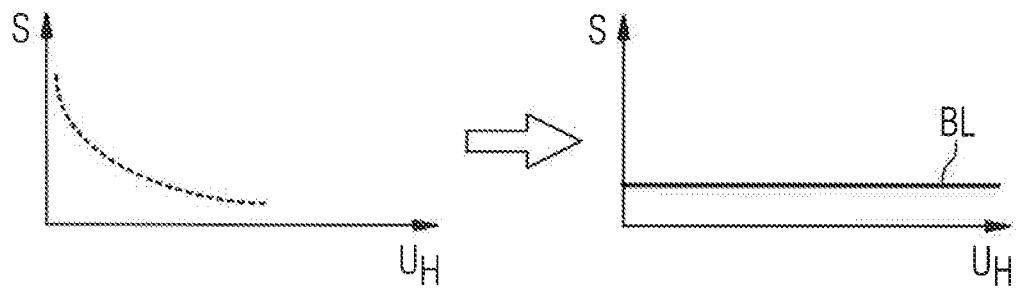
FIGS. 7 to 9 show graphs illustrating aspects of the method for operating the sensor device according to further embodiments.

In order to separate the poisoning effect from gas-change-induced changes of the temperature sensor element reading, as explained above a temperature sweep is performed in method step 101 of the method of FIG. 1, and a plurality of measurements is taken. Since the output signal of the temperature sensor elements is typically not linear and has, for example, for a thermistor material a negative temperature dependence with increasing temperatures as shown in FIG. 7 in the left graph, a calibration can be done in a clean gas as clean air and in the absence of a poisoning layer. The calibration can be done by measuring the temperature sensor element reading for different heater settings and by using this temperature-dependent behavior for defining a baseline. Consequently, the calibrated temperature sensor element reading can be characterized by the baseline BL, which corresponds to a constant value independent of the heater setting, as shown in FIG. 7 in the graph on the right-hand side. If shifts in the baseline are measured, they can be caused by changes in the gas atmosphere and/or a drift due to the poisoning effect.

FIG. 8 shows again a schematic non-linear and not steadily rising ideal behavior as explained in connection with FIGS. 5A and 5B. For illustrative reasons, also the baseline BL is shown, which corresponds to the horizontal axis in FIGS. 5A and 5B. In contrast to the ideal behavior, due to the cooling effect, which is stronger for higher temperature gradients between the pellistor element(s) and the surroundings, the poisoning effect leads to a drift that is steadily rising or falling as shown in FIG. 9 and as explained above. The steadily rising or falling function can be linear, as indicated by the continuous line, or polynomial, as indicated by the dashed line, or exponential or can be a combination thereof. The cross in FIGS. 8 and 9 indicates a certain temperature sensor element reading, which could be caused by the gas atmosphere and/or by the poisoning effect. Therefore, at a single measurement temperature and thus with a single heater setting it is impossible to distinguish between the poisoning effect and the influence of the gas.

Figure 8:
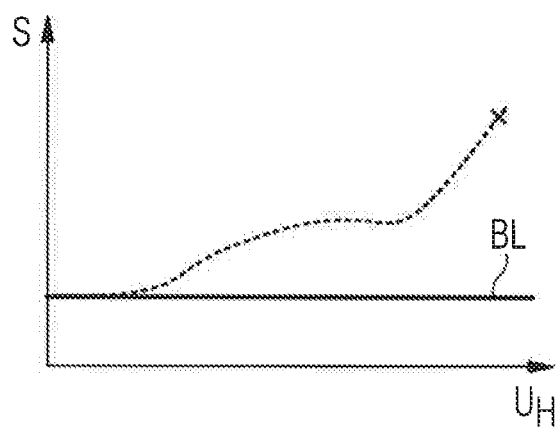
Figure 9:
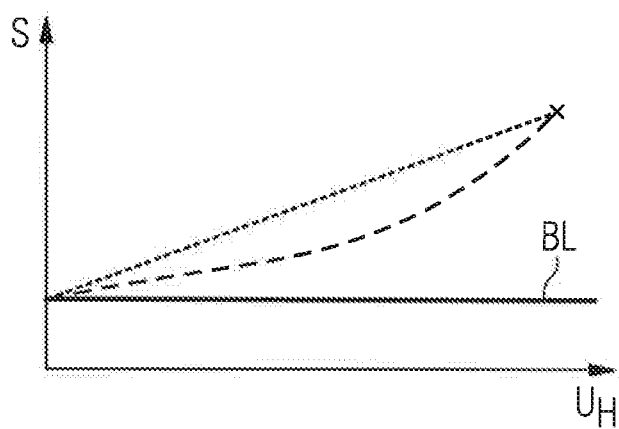

With regard to method step 102 of the method of FIG. 1, the first function can be based on a behavior as shown in FIGS. 5A, 5B and 8, which characterizes an ideal behavior of the pellistor elements and thus of the sensor device. The second function can be based on a steadily rising or falling function as shown in FIG. 9. By sweeping to different temperatures by changing the heater settings for performing the measurements of method step 101 and by performing the curve fitting of method step 102, it is possible to separate both effects, as during the temperature sweep both effects differently contribute to the temperature sensor element reading. As the dependencies of the ideal behavior and the poisoning effect look quite different, the curve fit could in principle be very accurate, so that even a contribution of 50% poisoning effect and 50% gas-induced contribution could be identified.

In order to increase the accuracy of the resistance measurement when measuring the temperature sensor element reading, the following embodiments could be useful in connection with the described method. If a thermistor is used as a temperature sensor element, the resistance can be as high as, for example, 10 MΩ at room temperature, going down to a value as low as, for example, 5 kΩ at 300° C. Therefore, it could be quite difficult to build a suitable ASIC for processing the resistance change. In an ideal case a voltage divider as described in connection with FIG. 4 should be used giving a constant output for all temperatures. If there is a gas exposure or change in gas composition there should be a difference in the constant voltage, although, as described above, also the poisoning-effect-caused drift will lead to a difference in the output voltage. It could be advantageous if the second pellistor element as a reference pellistor element is operated in clean air or vacuum to establish the desired behavior. Both pellistor elements can be operated with the same heater settings, so that the heater elements could be biased by the same supply voltage, allowing a simultaneous temperature sweep. As both pellistor elements react in the same way to temperature changes in an ideal case there is only the gas information included in the voltage divider output. If there is a little temperature difference between the pellistor elements, this could be canceled by a temperature calibration. Another possibility can be the use of a second pellistor element, which has a different temperature characteristic compared to the first pellistor element. The second pellistor element can be constructed in such a way that it will heat to a lower temperature when applying as a heater setting the same voltage as to the first pellistor element. For example, a typical heating voltage of 2.3 V could lead to a temperature of about 100° C. of the reference pellistor element and to a temperature of about 300° C. of the active pellistor element. The temperature sensor element of the reference pellistor element can be constructed in such a way that it has nearly the same resistance dependence with regard to the heater setting as the temperature sensor element of the active pellistor element. For instance, the temperature sensor element could have a resistance of 5 kΩ at 100° C., while the temperature sensor element of the active pellistor element could have a resistance of 5 kΩ at 300° C. With such a setup, it can be possible to cancel small heating voltage variations during the temperature sweep. Furthermore, it can be possible that it is not necessary to perform a complete temperature sweep. It could be sufficient to measure a fixed number of temperatures, for example, at 30° C., 150° C. and 300° C., and develop a mathematical model for this.

Alternatively or additionally to the features described in connection with the figures, the embodiments shown in the figures can comprise further features described in the general part of the description. Moreover, features and embodiments of the figures can be combined with each other, even if such combination is not explicitly described.

The invention is not restricted by the description on the basis of the exemplary embodiments. Rather, the invention encompasses any new feature and also any combination of features, which in particular comprises any combination of features in the patent claims, even if this feature or this combination itself is not explicitly specified in the patent claims or exemplary embodiments.

What is claimed is:

1. A method for operating a sensor device for measuring a concentration of a gas species in a gas, wherein the sensor device comprises a first pellistor element in contact with the gas, and wherein the first pellistor element comprises a heater element and a temperature sensor element, the method comprising:
    recording a set of data points by performing a plurality of measurements of a temperature sensor element reading, wherein each of the measurements is performed with a different heater setting of the first pellistor element and each of the measurements results in a data point of the set of data points;
    performing a curve fit of an evaluation function to the set of data points, wherein the evaluation function comprises a first function and a second function, wherein the first function is based on a baseline calibration of the first pellistor element, and wherein the second function is a temperature-dependent steadily rising or steadily falling function; and determining the concentration of the gas species in the gas from the curve fit.

2. The method according to claim 1, wherein the first function is different from a steadily rising or steadily falling function.

3. The method according to claim 1, wherein the second function takes into account a poisoning effect.

4. The method according to claim 1, wherein different heater settings correspond to different heating voltages and/or different heating currents applied to the heater element.

5. The method according to claim 1, wherein each of the data points comprises a calibrated temperature sensor element reading.

6. The method according to claim 1, wherein the sensor device comprises a second pellistor element having a heater element and a temperature sensor element, wherein the second pellistor element is a reference pellistor element, and wherein the method comprises:

operating the second pellistor element simultaneously to the first pellistor element while recording the set of data points, wherein performing the plurality of measurements of the temperature sensor element reading includes measuring a differential signal of an output of the temperature sensor element of the first pellistor element and of an output of the temperature sensor element of the second pellistor element.

7. The method according to claim 6, wherein the first pellistor element and the second pellistor element are embodied in the same way and operate with the same heater settings, and wherein the second pellistor element is operated in clean air or in vacuum.

8. The method according to claim 6, wherein for each measurement the heater element of the first pellistor element heats the first pellistor element to a first temperature and the heater element of the second pellistor element heats the second pellistor element to a second temperature that is different from the first temperature, and wherein the temperature sensor elements of the first and second pellistor elements are configured such that the temperature sensor element of the first pellistor element provides an output at the first temperature that is similar to an output of the temperature sensor element of the second pellistor element at the second temperature.

9. The method according to claim 8, wherein the second pellistor element is in contact with the gas at least while recording the set of data points.

10. The method according to claim 1, wherein the heater element is the temperature sensor element.

11. The method according to claim 1, wherein the heater element and the temperature sensor element are different components of the first pellistor element.

\* \* \* \* \*